United States Patent [19]

Young, Jr. et al.

[11] Patent Number: 5,013,860

[45] Date of Patent: May 7, 1991

[54] OXYDEHYDROGENATION OF DINITRILES

[75] Inventors: Harold W. Young, Jr., Baton Rouge, La.; William P. Dianis, Midland, Mich.

[73] Assignee: The Dow Chemical Company, Midland, Mich.

[21] Appl. No.: 267,474

[22] Filed: Nov. 4, 1988

Related U.S. Application Data

[63] Continuation-in-part of Ser. No. 193,440, May 12, 1988, which is a continuation of Ser. No. 859,179, May 2, 1986, abandoned.

[51] Int. Cl.$^5$ ............................................. C07C 253/30
[52] U.S. Cl. ................................................... 558/383
[58] Field of Search ........................................ 558/383

[56] References Cited

U.S. PATENT DOCUMENTS

| | | | |
|---|---|---|---|
| 2,399,349 | 4/1946 | Hochwalt | 260/464 |
| 2,434,606 | 1/1948 | Carpenter | 260/464 |
| 2,438,019 | 3/1948 | Pace | 260/465.2 |
| 2,442,319 | 5/1948 | Britton et al. | 260/680 |
| 2,442,320 | 5/1948 | Britton et al. | 260/680 |
| 2,456,367 | 12/1948 | Britton et al. | 252/228.2 |
| 2,456,368 | 12/1948 | Britton et al. | 252/228.2 |
| 2,471,767 | 5/1949 | Mowry et al. | 260/465.8 |
| 2,542,813 | 2/1951 | Heath | 23/105 |
| 2,701,260 | 2/1955 | Hagemeyer, Jr. | 260/465.9 |
| 2,904,580 | 9/1959 | Idol, Jr. | 260/465.3 |
| 3,308,190 | 3/1967 | Bajars | 260/680 |
| 3,308,193 | 3/1967 | Bajars | 260/680 |
| 3,308,197 | 3/1967 | Bajars | 260/680 |
| 3,308,198 | 3/1967 | Bajars | 260/680 |
| 3,308,199 | 3/1967 | Bajars | 260/680 |
| 3,308,200 | 3/1967 | Bajars | 260/680 |
| 3,313,840 | 4/1967 | Kosel et al. | 260/465.8 |
| 3,446,865 | 5/1969 | Roth et al. | 260/669 |
| 3,466,318 | 9/1969 | Lambert et al. | 260/465.9 |
| 3,625,647 | 12/1971 | Stowe | 23/105 |
| 3,641,180 | 2/1972 | Stowe et al. | 260/669 |
| 3,649,560 | 3/1972 | Croce et al. | 252/432 |
| 3,819,578 | 6/1974 | Schmidt, deceased et al. | 260/465.8 R |
| 3,851,008 | 11/1974 | Stowe et al. | 260/680 E |
| 3,907,916 | 9/1975 | Soderquist et al. | 260/669 R |
| 3,935,126 | 1/1976 | Vrieland | 252/437 |
| 3,959,345 | 5/1976 | Morita et al. | 260/465.8 R |
| 4,221,738 | 9/1980 | Imai | 260/465.9 |
| 4,375,571 | 3/1983 | Hart et al. | 585/431 |
| 4,436,671 | 3/1984 | Furuoya et al. | 260/465.3 |

FOREIGN PATENT DOCUMENTS

| | | |
|---|---|---|
| 1127890 | 4/1962 | Fed. Rep. of Germany . |
| 38-22563 | 10/1963 | Japan . |
| 4217965 | 9/1967 | Japan . |
| 44-15765 | 7/1969 | Japan . |
| 45-23523 | 8/1970 | Japan . |

*Primary Examiner*—Joseph Paul Brust

[57] ABSTRACT

Included is the oxydehydrogenation of saturated dinitriles, for example, succinonitrile, to prepare unsaturated dinitriles, for example, fumaronitrile and maleonitrile. Succinonitrile can be oxydehydrogenated by passing it in a vapor phase over a calcined calcium nickel phosphate catalyst, and the selectivity to fumaronitrile can be varied by the presence of water vapor in the vapor phase feed mixture.

15 Claims, No Drawings

OXYDEHYDROGENATION OF DINITRILES

CROSS-REFERENCE TO RELATED APPLICATIONS

This application is a continuation-in-part of co-pending application, Ser. No. 193,440, filed May 12, 1988 which is a continuation of application Ser. No. 859,179, filed May 2, 1986, now abandoned.

FIELD OF THE INVENTION

This invention concerns a process for oxydehydrogenation of relatively saturated dinitriles to produce relatively unsaturated dinitriles. Unsaturated dinitriles such as, for example, fumaronitriles and maleonitriles are useful monomers, especially as comonomers with styrene.

BACKGROUND OF THE INVENTION

Certain processes for the production of a dinitrile product such as a fumaronitrile or maleonitrile product are known. One, for example, involves oxydehydrogenation.

Kosel et al., U.S. Pat. No. 3,313,840 (1967) disclose a catalytic oxydehydrogenation process for the production of fumaro- and maleonitrile from succinonitrile. The process must be carried out in the presence of at least one oxide which is stable at the reaction temperature of an element of Groups Vb or VIb of the Periodic system, especially vanadium pentoxide, molybdenum trioxide and, particularly, chromium (III) oxide. It is disclosed that the dinitriles are produced in a practically constant ratio of fumaronitrile to maleonitrile of 5:4. A problem with this process can be the frequent regeneration or replacement of the catalyst.

Other processes for the production of a dinitrile product such as a fumaronitrile or maleonitrile product are also known. They generally fall into seven representative types.

The first is dehydration of a diamide of fumaric or maleic acids with phosphorous pentoxide such as taught by Pace, U.S. Pat. No. 2,438,019 (1948). Problems with this include difficulty in synthesizing the reactant diamide and the practical control of the strict reaction conditions.

The second is a 1,2-diiodoethylene and copper cyanide reaction such as taught by Hochwalt, U.S. Pat. No. 2,399,349 (1946). A problem with this is the procurement of special starting materials.

The third is an acetonitrile high temperature dehydrogenation-dimerization with chlorine such as taught by Japanese Patent Publication No. 17965/1967. Problems with this include the practical control of the strict reaction conditions and the corrosive nature of the reaction.

The fourth is a cyanoacetylene and prussic acid reaction such as taught by Morita et al., U.S. Pat. No. 3,959,345 (1976). A problem with this is the procurement of starting materials.

The fifth is oxycyanation, which is a 3-cyano-1-propene and cyanide reaction in the presence of oxygen such as taught by Kominomi et al., Kogyo Kogaku Zasshi, 74, 2464-68 (1971). Problems with this include low selectivity and catalyst coking.

The sixth is a fumaronitrile preparation by a chloroacrylonitrile and aqueous alkali or alkaline earth cyanide reaction such as taught by Mowry et al., U.S. Pat. No. 2,471,767 (1949). A problem with this is procurement of starting materials and strict reaction conditions.

The seventh is ammoxidation, a process involving an unsaturated compound, ammonia and oxygen. Proposed unsaturated compounds include benzene, cyclohexene, phenol and butadiene such as disclosed by Furuoya et al., U.S. Pat. No. 4,436,671 (1984). Problems with this include production of by-products such as acrylonitrile, acetonitrile and prussic acid.

In addition, the foregoing processes are typically restricted to preparing narrow classes of products, often only the compounds fumaronitrile and maleonitrile. Most are not readily commercially adaptable.

What is lacking and what is needed is a process for preparing a dinitrile product which is simple and direct, a process in which selectivity can be varied by varying process parameters and a process which may prepare a wide variety of dinitriles including, for example, fumaro- and maleonitriles. What is also lacking and what is needed is such a process which may be readily commercializable.

SUMMARY OF THE INVENTION

The invention is a process for preparing unsaturated dinitriles comprising oxydehydrogenating a saturated dinitrile in the presence of an oxydehydrogenation catalyst selected from the group consisting of a bismuth phosphomolybdate catalyst, an alkaline earth metal nickel phosphate catalyst, a chromium oxide alkaline earth metal nickel phosphate catalyst and a transition metal molybdate catalyst under conditions whereby the unsaturated dinitrile is prepared. Optionally, the catalyst additionally contains an alkali metal promoter present in an amount of no greater than about 20 weight percent based on the weight of the catalyst plus promoter.

The process is simple, direct and can be used to prepare a wide variety of unsaturated dinitriles, including fumaro- and maleonitriles (i.e., fumaronitrile, maleonitrile, 2,3-disubstituted fumaronitriles and 2,3-disubstituted maleonitriles). The product distribution can be varied by the specific catalyst compound employed and by other process parameters such as operating conditions and diluents co-fed with the saturated dinitriles, including succinonitriles. The process is efficient, the starting materials are easily obtainable, and the process may be readily commercializable, especially because of this.

The reaction often produces relatively few by-products. The major by-product of the process is water.

It is surprising that the process of the present invention results in the efficient production of the unsaturated dinitriles, particularly fumaronitrile and maleonitrile, by the oxydehydrogenation of succinonitrile. While it is known that unsaturated mononitriles may be prepared by catalytic oxydehydrogenation, it is surprising that unsaturated dinitriles rather than compounds containing more than one organic moiety such as nitrile plus aldehyde or nitrile plus amide are readily prepared using the process of this invention.

The unsaturated dinitriles are useful as starting materials for various useful chemicals and for polymers. For example, the fumaronitriles and maleonitriles are useful as starting materials for various medicines, industrial chemicals or polymers. Polymeric use can be as a comonomer in copolymerizations with other unsaturated monomers. The presence of substituted functionalities of the relatively unsaturated dinitriles, including 2,3- disubstituted fumaronitriles and 2,3-disubstituted maleonitriles may be taken advantage of in use.

ILLUSTRATIVE EMBODIMENTS

In general, the saturated dinitriles which can be oxydehydrogenated by the process of the invention include compounds of the formula

$$N \equiv C(CR^1{}_2)_m CHR^2 - CHR^3 (CR^1{}_2)_m C \equiv N \quad (I)$$

wherein m is separately at each occurrence an integer from zero to about 5: and $R^1$, $R^2$ and $R^3$ are separately at each occurrence hydrogen, a $C_{1-20}$ alkyl, aryl, aralkyl, alkylaryl or alicyclic hydrocarbyl or a substituted $C_{1-20}$ alkyl, aryl, aralkyl, alkylaryl or alicyclic hydrocarbyl substituent.

The organic moieties, $R^1$, $R^2$ and $R^3$, are generally inert. By inert, it is meant that they are such that they do not prevent formation of the product by the oxydehydrogenation. These $C_{1-20}$ hydrocarbyl moieties may additionally be substituted with one or more hydroxyl, carbonyl or ether groups.

Preferably, $R^1$, $R^2$ and $R^3$ are separately at each occurrence hydrogen or $C_{1-20}$ hydrocarbyl, more preferably hydrogen, $C_{1-12}$ aryl, arylalkyl, alkylaryl or alkyl and most preferably hydrogen, methyl or ethyl, especially hydrogen. It is preferred that the dinitriles be volatile enough to be fed to the catalyst site in the vapor phase, as is the compound succinonitrile.

Preferably, m is zero. Thus, preferred saturated dinitriles are succinonitrile and substituted succinonitriles.

The succinonitriles include compounds of the formula

$$N \equiv C - CHR^2 - CHR^3 - C \equiv N \quad (II)$$

wherein $R^2$ and $R^3$ are as defined above.

It is especially preferred that $R^2$ and $R^3$ are hydrogen. Thus, the compound succinonitrile is especially preferred among the succinonitriles.

The saturated dinitriles are readily obtainable or may be prepared by known methods. One preferred method to prepare succinonitriles, for example, is by the teachings of Carpenter, U.S. Pat. No. 2,434,606 (1948) (incorporated herein by reference). A preferred method to obtain the compound succinonitrile is by the reaction of acrylonitrile and HCN in the presence of base such as an alkali metal hydroxide (e.g., NaOH, KOH) or tertiary amines (e.g., triethylamine).

The unsaturated dinitriles have a ratio of carbon to hydrogen which is greater than the carbon to hydrogen ratio of the appropriately corresponding saturated dinitriles because of the removal of hydrogen by the oxydehydrogenation. Thus, the relatively unsaturated dinitriles can include compounds of the formula

$$N \equiv C + CR^1{}_2 +_m CR^2 = CR^3 + CR^1{}_2 +_m C \equiv N \quad (III)$$

When m is not zero, the unsaturated dinitriles prepared by this process of this invention may include additional ethylenic unsaturation. Preferably, m is zero and the unsaturated dinitriles prepared by the process of this invention are fumaronitrile and maleonitrile and substituted fumaronitriles and maleonitriles. The fumaronitriles prepared by the process of this invention include compounds corresponding to the formula

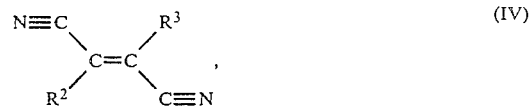

and the maleonitriles include compounds corresponding to the formula

wherein $R^2$ and $R^3$ are as defined above. Preferably, $R^2$ and $R^3$ remain the same before and after reaction. Thus, it is most preferred that fumaronitrile and maleonitrile are prepared from the catalytic oxydehydrogenation of succinonitrile.

Oxydehydrogenating means the saturated dinitriles undergo loss of at least two hydrogen atoms to produce the unsaturated dinitriles while simultaneously producing water. Preferably, two hydrogen atoms are given up by each of the saturated dinitriles, especially the succinonitriles, to produce the corresponding unsaturated dinitriles, especially the fumaronitriles or maleonitriles.

Oxygen is employed in the process. Preferred sources of oxygen include sources of elemental oxygen such as in pure $O_2$ or in oxygen-containing atmospheres, preferably having an oxygen content of about 30 mole percent or below. Most preferably, the oxygen content of the oxygen-containing atmosphere is from about 1 mole percent to about 22 mole percent. The oxygen content of the oxygen-containing atmosphere can be maintained at or below about 7 mole percent in order to minimize any risk of a runaway reaction. Gaseous components other than $O_2$ in the oxygen-containing atmosphere can include other sources of elemental oxygen such as nitrous oxide and can include gaseous diluents such as water vapor, elemental nitrogen, helium and argon. Small amounts of $CO_2$ and the like are not typically detrimental. More preferably, the gaseous components other than $O_2$ in the oxygen-containing atmosphere are substantially $N_2$, water vapor or other gaseous components such as would be typically found in air.

In one embodiment, the oxydehydrogenation catalyst is a heterogeneous, solid catalyst containing phosphorus, oxygen, an alkaline earth metal, Ni, Bi, Mo and Cr, etc. and may be additionally calcined before use The oxydehydrogenation catalyst can be unsupported, or supported by a solid oxide, or comprise a binder. The catalyst is an alkaline earth, Ni, P-containing catalyst such as disclosed by Britton et al., U.S. Pat. Nos. 2,442,319 (1948): 2,456,367 (1948): Heath, U.S. Pat. No. 2,542,813 (1951): and Stowe, U.S. Pat. No. 3,624,647 (1971) (each incorporated herein by reference), which is termed "Type DA" (i.e., Dow Chemical Type A) when the alkaline earth therein is primarily calcium. The Type A catalyst can be additionally impregnated with phosphate ions such as disclosed by Vrieland, U.S. Pat. No. 3,935,126 (1976) (incorporated herein by reference), which catalyst is termed "Type DAP" (i.e., Dow Chemical Type AP). In general, the Type DA which additionally contains a promoter such as chromium (preferably at levels of from about 0.1 to about 10 weight percent) such as disclosed by Britton et al., U.S. Pat. Nos. 2,442,320 (1948): 2,456,368 (1948) (both incorporated herein by reference), is also preferred and is termed "Type DB" (i.e., Dow Chemical Type B). When the alkaline earth metal component of the alkaline earth, Ni, P-containing catalyst is primarily strontium such as disclosed by Stowe 30 et al., U.S. Pat. No. 3,641,180 (1972) and Stowe et al., U.S. Pat. No. 3,851,008 (1974) (both incorporated herein by reference), the catalyst is termed "Type DS" (i.e., Dow Chemical Type S). The catalyst may also be a Bi, Mo-containing catalyst is such as disclosed by Idol, Jr., U.S. Pat. No. 2,904,580 (1957) (incorporated herein by reference), which is termed "Type SA" (i.e., Sohio Type A) or preferably, a bismuth phosphomolybdate catalyst. The alkaline earth, Ni and P-containing catalysts are preferred, especially when unsupported. The following table illustrates these catalyst embodiments.

| Type | General Preparation |
|------|---------------------|
| DA | $8CaCl_2 + NiCl_2 + 6H_3PO_4 + 18NH_3 \rightarrow Ca_8Ni(PO_4)_6$ |
| DB | DA + 3 weight percent $Cr_2O_3$ $\rightarrow Ca_8Ni(PO_4)_6/3\% \ Cr_2O_3$ |
| DS | $5Sr(OH)_2 + NiCl_2 + 3H_3PO_4 + NH_4(H_2PO_4) \rightarrow Sr_5Ni(PO_4)_4$ |
| SA | $1.9MoO_3 + 0.67HNO_3 + 1.2Bi(NO_3)_3 + 0.14H_3PO_4$ + about 20 weight percent silica $\rightarrow$ Type SA |

Preferably, the catalyst is calcined before use. The calcination is preferably carried out in flowing air at temperatures from about 200° C. to about 800° C. for from about 1 to 24 hours. Most preferably, the calcination is carried out, in the presence of water vapor, at from about 600° C. to about 700° C. for about 4 to 8 hours. Most preferably, calcination of the Dow Type A, AP, B and S catalysts is carried out for about 6 hours at about 650° C. with about 2.5 cm per minute of air and about 0.6 g per hour of water vapor per 1.0 cm of catalyst.

In an additional embodiment, the oxydehydrogenation catalyst comprises a heterogeneous, solid catalyst comprising a molybdate functionality comprising oxygen and molybdenum, and at least one additional transition metal. Preferably, the oxydehydrogenation catalysts useful in this embodiment of the invention comprise a compound corresponding to the formula $$A_aB_bC_cD_dE_eMo_mO_x$$

wherein

A represents a Group IIB metal, preferably zinc, and a is at least 0 and no greater than about 1;

B represents a Group IIIB metal, preferably lanthanum, and b is at least 0 and no greater than about 4;

C represents bismuth or antimony, preferably bismuth, and c is at least 0 and no greater than about 4;

D represents iron, cobalt, nickel or cadmium, preferably iron, and d is at least 0 and no greater than about 4;

E represents a lanthanide, preferably cerium, and e is at least about 0 and no greater than about 2;

Mo represents molybdenum and m is greater than zero and less than or equal to 3: and 0 represents oxygen and x is equal to 0.5 times the sum of the products of "a" times the valency of A plus "b" times the valency of B plus "c" times the valency of C plus "d" times the valency of D plus "e" times the valency of E:

with the proviso that at least one of a, b, c, d, and e is above zero.

The compounds corresponding to the above formula comprise crystalline molybdates, solid solutions, mixtures of crystalline phases, mixtures of crystalline and amorphous phases, and mixtures of molybdates and oxides where the molybdate is the largest single component by weight.

Examples of preferred compounds useful as transition metal molybdate catalysts in this embodiment of the invention include $Bi_2Mo_3O_{12}$, $Bi_3FeMo_2O_{12}$, $ZnMoO_4$, $Bi_2Fe_2Mo_2O_{12}$, $Bi_{1.8}Ce_{0.2}Mo_3O_{12}$, $Bi_{0.875}Ce_{1.125}Mo_3O_{12}$, $La_2Mo_3O_{12}$, $Bi_4ZnMo_3O_{16}$, $NiMoO_4$, $Ce_2Mo_3O_{12}$, $CoMoO_4$, and $Sb_2MoO_6$.

The transition metal molybdate catalysts may be made by methods known in the art. For example, the catalysts may be prepared by co-precipitation or by fusion of oxides.

The transition metal molybdate catalysts useful in the process of this invention are preferably unsupported. However, binders are useful in the preparation of the catalysts. Materials useful as binders are those which provide adequate strength to the catalysts for handling and processing. Binder materials useful in the catalysts do not make significant contributions to undesired side reactions. For example, such binder materials do not significantly contribute to reactions such as cracking or complete combustion. Non-limiting examples of materials useful as binders in the practice of this invention include silica, titania, aluminum phosphate, kaolin clay, montmorillonite clay, attapulgite clay and Portland cement. A preferred binder is kaolin clay.

The binder is mixed with the calcined catalyst in an amount to impart sufficient strength to the catalyst to facilitate handling and processing. It is preferred that the binder constitute at least about 1 weight percent of the total catalyst including binder and more preferred that it constitute at least about 10 weight percent. It is also preferred that the binder constitute no more than about 60 weight percent of the total catalyst including binder and more preferred that it constitute no more than about 30 weight percent. It is most preferred that the binder constitute about 20 weight percent.

Preferably, the transition metal molybdate catalyst is calcined before use. The calcination is carried out in flowing air at temperatures from about 200° C. to about 800° C. for from about 1 to 24 hours. Most preferably, the calcination is carried out in air at a temperature of about 200° C. for from about 2 to about 5 hours after which the temperature is increased to a temperature of from about 400° C. to about 600° C. and maintained at the higher temperature for from about 10 hours to about 16 hours. When the calcined catalyst is mixed with a binder, the catalyst/binder is then calcined again. The second calcination is preferably done in air at from about 175° C. to 225° C. for a period of from about 1.5 to 2.5 hours and then the temperature is raised to from about 450° C. to 550° C. for an additional 3 to 5 hours.

The catalysts useful in the oxydehydrogenation process of the present invention may additionally comprise an alkali metal, preferably potassium, sodium or cesium. It is more preferred that the alkali metal is potassium. When the alkali metal is used, it is preferred to dry blend an alkali metal salt with the calcined catalyst powder and then mix this with an appropriate binder and then calcine the catalyst with the alkali metal and the binder.

The alkali metal is used in any amount which will result in increased conversion and/or improved selectivity. It is preferred to use the alkali metal in an amount such that the alkali metal will constitute at least about 0.10 weight percent based on the total weight of the catalyst and binder, if any, and more preferred that the alkali metal constitute at least about 1.0 weight percent. It is also preferred that the alkali metal constitute no more than about 20 weight percent, more preferably about 10 weight percent and most preferably about 5 weight percent of the total weight of the catalyst and binder, if any.

The conditions of the process are those sufficient to prepare the unsaturated dinitrile product. A combination of unsaturated dinitrile products may be prepared.

Preferred conditions include vapor phase feed of the saturated dinitriles to the catalytic site. Preferably, the saturated dinitriles are contacted with and carried in the feed which is itself an oxygen-containing atmosphere. However, liquid phase reactions, especially with higher molecular weight reactants and products, may be employed.

The oxygen to saturated dinitriles (reactant dinitriles) molar ratio is any which is sufficient to prepare the relatively unsaturated dinitriles (product dinitriles). The preferred lower limit of this ratio (as if the oxygen is molecular oxygen) is from about 0.01:1, more preferably from about 0.1:1 and most preferably from about 0.5:1. The preferred upper limit is from about 10:1, more preferably from about 5:1 and most preferably from about 3:1.

The reactant dinitriles often can be advantageously mixed into the vapor phase feed mixture from a liquid phase because of the usually higher vapor pressure of the liquid in comparison to a solid at preferred operating conditions. However, sublimation of solid reactant dinitriles may also be employed to obtain the vapor phase feed mixture, often advantageously at lower pressures.

Preferably, the reactant dinitrile is fed at moderate or lowered temperatures. To accomplish the lower temperatures of the liquid phases while keeping the volatility of the reactant dinitriles at acceptable levels, liquid diluents may be employed. The liquid phase may be a solution or a heterogeneous mixture such as multiple immiscible liquid phases, suspensions or an emulsion where an emulsifying agent may be additionally employed. Liquid diluents can include acetone, chlorinated hydrocarbons, for example, $CCl_4$, toluene and acetonitrile, and water. Water is an especially preferred liquid diluent, most especially with the compound succinonitrile. The liquid diluent/reactant dinitriles mixture is preferably at levels near concentrations of each component at which a saturated liquid solution is mixed into the vapor phase feed mixture. For example, with the liquid diluent water and the compound succinonitrile, a preferred liquid mixture of these components at about normal temperature and pressure (i.e., NTP, which is about 21° C and one atmosphere) is about 8 weight percent water and 92 weight percent succinonitrile which is near the eutectic ratio. Of course, varying of the temperature and pressure of the diluted reactant dinitriles, and varying the components of the mixture such as by addition of other components, can be used to vary the ratio of the reactant dinitriles feed, especially as a eutectic mixture.

Water is preferably present in the vapor phase feed mixture because it preferably aids the catalysis of the reaction. In addition, when the catalyst is one such as the alkaline earth, Ni, P-containing catalysts, including those containing components such as chromium, the presence of water vapor in the vapor phase feed mixture can be employed to vary the ratio of product dinitrile isomers such as fumaronitriles to maleonitriles in the product. For example, with a helium feed mixture diluent in the oxydehydrogenation of the compound succinonitrile, the fumaronitrile fraction of the desired product is typically from about 45 to about 55 percent by weight (e.g., 50 percent) whereas with water vapor as the diluent, the fumaronitrile fraction can be increased to from about 55 to about 65 percent (e.g., 58 to 63 percent). In contrast, with the Type SA catalysts, with water vapor as the vapor phase feed mixture diluent, only a few percent of the desired unsaturated dinitriles are typically prepared which is accompanied by about 20 percent of an unidentified by-product. Thus, preferred lower levels of the range of water in the vapor phase feed are about 0.1 weight percent of the vapor phase feed, more preferably about 1 weight percent and most preferably about 3 weight percent. When the oxydehydrogenation catalyst is such as the Type DA, DAP, DB and DS, preferred upper levels of the range of water in the vapor phase feed are about 98 weight percent of the vapor phase feed, more preferably about 95 percent and most preferably about 90 percent. However, with catalysts such as the Type SA, preferred upper levels of the range of water in the vapor phase feed are about 20 weight percent of the vapor phase feed, more preferably about 15 percent and most preferably about 10 percent. Similarly, when the transition metal molybdate type catalysts are used, it is preferred that the upper levels of the range of water in the vapor phase feed are about 35 percent.

It should be noted that while the amount of fumaronitrile relative to maleonitrile can be increased when water is used as a co-diluent in the vapor phase feed with the alkaline earth metal, nickel, phosphorus containing catalysts and transition metal molybdate catalysts, the overall selectivity to the dinitrile products may be decreased.

An induction effect, whereby the conversion increases with the time of the catalyzed reaction, can occur with certain catalysts under certain conditions. For the most part, the induction effect is related to the vapo phase diluent and the catalyst employed.

Preferably, the reactant dinitriles are oxydehydrogenated at elevated temperatures. Elevated temperatures include temperatures about 50° C. and above. Preferred lower limits of the elevated temperature range of the reaction are about 300° C., more preferably about 330° C. and most preferably about 350° C. Preferred upper limits of the elevated temperature range of the reaction are about 650° C., more preferably about 600° C. and most preferably about 500° C.

Preferred lower limits of range of the pressure of the reaction are about 0.01 atmospheres (1.0 kPa), more preferably about 0.1 atmospheres (10.1 kPa) and most preferably about 0.5 atmospheres (50.5 kPa). Preferred upper limits of the range of the pressure of the reaction are about 100 atmospheres (10,100 kPa), more preferably about 10 atmospheres (1,010 kPa) and most preferably about 3 atmospheres (303 kPa).

Preferably, the reaction vessel is generally inert to the reaction or even aids in effecting it. Preferred reaction vessels include those such as of stainless steel or glass.

An exotherm within the catalyst bed is typically present during the oxydehydrogenation. The exotherm can be as much as 40° C. Reactor configurations and operating conditions are preferably chosen to minimize this phenomenon. For example, a tube-and-shell reactor can be used, with catalyst packed in the tubes and a heat-transferring means such as, for example, steam, an organic heat-transfer fluid or molten salt bath, circulated on the shell side. Or, a fluidized bed reactor may be employed. Other reactor configurations will be apparent to those skilled in the art.

When running the reaction as a vapor phase carried oxydehydrogenation, preferred lower limits of the range of rates of passing the vapor phase feed mixture (measure by liquid hourly space velocity of liquid or liquefied reactant dinitrile) over the heterogeneous oxydehydrogenation catalysts (grams per hour per cm of catalyst) are at liquid hourly space velocities of from about 0.001 per hour, more preferably from about 0.01 per hour and most preferably from about 0.1 per hour. Equivalent preferred upper limits are about 50 per hour, more preferably about 10 per hour and most preferably about 3 per hour. Of course, the most preferred feed space velocities can vary with the oxydehydrogenation catalyst and the other reaction conditions employed, for example, temperature, amounts of oxygen and reactant dinitriles present, and recycle of unreacted feed.

In a flow-type reaction, the recycle ratio is the ratio of moles of nitrile-compound effluent returned to the feed, to the moles of fresh reactant dinitriles in the feed. Recycle ratios may vary from zero to any number which results in the formation of product. Preferably, unreacted feed is recycled, more preferably in vapor phase feeding at a recycle ratio from about 0.1 to about 10. Typically, the desired product is removed from the effluent before recycle.

Conversion of the reactant dinitriles to the product dinitriles is a function of the reaction conditions, reactants, and oxydehydrogenation catalyst employed. Within the preferred temperature ranges, as temperature increases the conversion generally increases. Within the preferred operating feed space velocity ranges, as the space velocity increases the conversion usually decreases.

Selectivity is the total mole percent of the reactant dinitriles converted, divided into the mole percent of types of desired product dinitriles. Thus, $$\text{Selectivity} = \frac{\text{Desired Product Dinitriles}}{\text{Total Reactant Dinitriles Converted}}.$$

Preferably, for example, selectivities of reactant dinitriles such as succinonitriles converted to desired product dinitriles such as maleonitriles plus fumaronitriles are 50 mole percent or above, more preferably about 58 mole percent or above and most preferably about 65 mole percent or above.

The product is collected by known methods. In liquid phase reactions, the product is readily collected in solid vessels. In gas-fed reactions, the product is preferably trapped such as by air-, water- or other-wise-cooled condensing apparatus and collected as a liquid or solid.

Purification of the product can be accomplished as desired by known methods. A preferred method is by the method of Kosel et al., U.S. Pat. No. 3,313,840 (1967) (incorporated herein by reference).

Typically, the products may be hygroscopic, and thus, water may appear in it. If desired, the water may be removed by known means, such as by distilling, chromatography and drying agents such as chemical drying agents, absorbents such as silica, and molecular sieves.

Also, when the reactant dinitrile is the compound succinonitrile, for example, frequently appearing in the product are trace amounts of acrylonitrile and acetonitrile. In addition, by-products such as ammonia, prussic acid and carbon oxides may be produced by "deep oxidation" of the succinonitriles. These, too, can be removed, if desired, by known methods such as distillation, chromatography, adsorbents such as activated carbon and molecular sieves, and recrystallization, as applicable.

SPECIFIC EMBODIMENTS

The following examples further illustrate the invention. In the examples, the reactants and diluents are of reagent grade, or higher, quality, unless otherwise noted. Percentages are by weight, unless otherwise noted.

EXAMPLE 1

Air (Scott: 21.0 percent oxygen) saturated with succinonitrile vapors at 105° C. is passed over 13.3 g of Type SA (Sohio A) catalyst (Standard Oil of Ohio) in a glass reactor 25 mm inside diameter at 380° C. at a flow rate of 35 scc/min. The effluent of the reactor is trapped and analyzed on a gas chromatograph. After 7 hours, the only organic compounds detected are succinonitrile (73.9 percent), fumaronitrile (18.5 percent) and maleonitrile (7.6 percent).

EXAMPLE 2

Air (Scott 21.0 percent oxygen) is saturated with succinonitrile vapors at 105° C. and is passed over 10.2 g of Type DAP (Dow Chemical Type AP) catalyst (as is prepared by the procedure of Example 1 of U.S. Pat. No. 3,935,126 (1976)) in a 25 mm inside diameter glass reactor at 60 scc/min. The reactor is heated to 460° C. The effluent is trapped for 6 hours. At the end of this time, the trap is washed with acetone, and the contents of the trap are analyzed by gas chromatography. Succinonitrile conversion is 79.9 percent, and the ratio of fumaronitrile to maleonitrile is 61.6:38.4.

EXAMPLE 3

Following the procedure of Example 1 and 2, the following is obtained under the other conditions listed. Dry $N_2$ is used to dilute the air which contains 21.0 percent oxygen. The Isomer Fraction is calculated by the quotient $$\frac{\text{Mass Fumaronitrile}}{\text{Mass Fumaronitrile} + \text{Mass Maleonitrile}}.$$

the flow rate is in units of standard cubic centimeters per minutes (i.e., scc/min) as corrected to STP. Runs C and G are measured at 7 hours on stream at the listed temperature. Runs A, B, D–F are measured at from 6–8 hours on stream. The results obtained are shown in Table I below.

TABLE I

| Run | Catalyst | Flow Rate (scc/min) | % $O_2$ | Temp (°C.) | % Conversion | Isomer Fraction |
| --- | --- | --- | --- | --- | --- | --- |
| A | Sohio A | 185 | 6.8 | 320 | 11.5 | 47.2 |

TABLE I-continued

| Run | Catalyst | Flow Rate (scc/min) | % O$_2$ | Temp (°C.) | % Conversion | Isomer Fraction |
|---|---|---|---|---|---|---|
| B | Sohio A | 100 | 7.4 | 340 | 20.9 | 69.7 |
| C | Sohio A | 35 | 21.0 | 380 | 26.1 | 70.9 |
| D | Dow AP | 60 | 21.0 | 450 | 46.2 | 41.8 |
| E | Dow AP | 120 | 3.5 | 440 | 33.3 | 34.8 |
| F | Dow AP | 60 | 21.0 | 410 | 26.2 | 39.3 |
| G | Dow AP | 60 | 21.0 | 430 | 45.0 | 43.3 |

EXAMPLE 4

The following runs are carried out in a ¾-inch (i.e. 1.90 cm) outside diameter, 0.62-inch (i.e., 1.57 cm) inside diameter, 30-inch (i.e., 76.2 cm) length, 316 stainless steel tube reactor. The tube contains 50 cm³ of 5-12 mesh (Tyler mesh designation, i.e., 1.41 mm to 4.00 mm) catalyst. The catalyst bed is 10 inches (i.e., 25.4 cm) in length, and it occupies the middle third of the reactor tube. Berl saddles, a catalytically inert ceramic, is packed above and below the catalyst. A ⅛-inch (i.e., 0.32 cm) thermowell is inserted inside the reactor, and the operating temperature is measured by sliding a type K thermocouple inside the thermowell. The reactor tube is placed inside a 30-inch long, 3-zone electric furnace. The zones are controlled separately, and the temperatures are adjusted so that the catalyst bed has a reasonably uniform temperature before the start of a run. The succinonitrile is added as a mixture of succinonitrile and water with a composition of about 87 percent succinonitrile and 13 percent water. When necessary, the feed is filtered to remove dark insoluble matter. The oil is fed to the reactor with a small positive displacement pump. A pressurized feed tank is suspended from a weigh cell and the feed rate is determined by recording the feed tank weight versus time. Optionally, water is co-fed to the reactor with a second pump. Gases are added to the reactor with electronic mass flow controllers. The inert gas diluent is He, and the oxygen gas is added from a premixed tank containing 20 percent oxygen and 80 percent helium at about 1-2 psig (i.e., gauge pressure of about 0.133 to about 0.266 kPa). This slight pressure is employed to circulate the noncondensed product gas through an online gas chromatograph. The product from the reactor is condensed and collected in a receiver. Samples are analyzed with a capillary gas chromatograph. Noncondensed products are directed to the online gas chromatograph which analyzes for oxygen, carbon monoxide, carbon dioxide, ammonia and nitrogen. The vent gas is directed through a caustic scrubber before being vented.

The alkaline earth, Ni, P-containing catalysts are unsupported. The catalysts have the following composition

| Catalyst | Support | Nominal Composition |
|---|---|---|
| DA | none added | Ca$_8$Ni(PO$_4$)$_6$ |
| DB | none added | 97% Ca$_8$Ni(PO$_4$)$_6$ + 3% Cr |
| DS | none added | Sr$_5$Ni(PO$_4$)$_4$ |

The Type SA catalyst as is obtained from Standard Oil of Ohio is a fine powder which is agglomerated before use. To agglomerate the Type SA catalyst, Ludox AS-40, a colloidal silica, is added to the catalyst to produce a moist cake. The cake is dried at 110° C., then is calcined in air at 400° C. for 2½ hours. The cake is then crushed to 5-12 mesh. The final Type SA catalyst contains 22 percent SiO$_2$ as a binder.

Calcination of the Type DA, DB and DS catalysts is carried out in a Lindberg furnace with 50 cm³ of catalyst. Air is passed over the catalyst sample at a flow rate of 125 cm per minute with water vapor at a flow rate of 60 g per hour. The temperature is raised from ambient temperature to 650° C. over the course of 2 hours, and the heating rate is held nearly constant up to the 650° C. temperature. The 650° C. temperature is maintained for 6 hours. The calcined catalyst is then allowed to cool to ambient temperature and then transferred to the above reactor. Conversion and selectivity are calculated by determining oxygen consumption with the vent gas analysis and consumption of oxygen to fumaro- and maleonitriles with the liquid analysis, using the following: SN is succinonitrile: FN is fumaronitrile; and MN is maleonitrile. By letting X be the proportion of converted SN which is converted to FN+MN, and (1) $X(SN + 1/2O_2) \rightarrow X(FN + H_2O)$ (2) $(1-X)(SN + 7/2O_2 +) H_2O \rightarrow (1-X)(4CO_2 + 2NJ_3)$ wherein step (1) is the oxydehydrogenation step, and step (2) is the "deep oxidation" loss. Then, by adding steps (1) and (2) and defining Δ as the total of moles O$_2$ fed in minus moles O$_2$ out; and f as moles O$_2$ consumed in the oxydehydrogenation, $$X = \frac{7(f/\Delta)}{1 + 6(f/\Delta)}.$$

The O$_2$ is added as 20 percent O$_2$/80 percent He mixture to simulate air. The He is employed for analytical purposes.

All percents in the following table are mole percent. Temperature is in degrees centigrade. Isomer Fraction is $$\frac{\% \, FN \, in \, product}{\% \, FN + \% \, MN \, in \, product} \times 100\%.$$

The O$_2$ conversion is $$\frac{O_2 \, consumed}{O_2 \, fed} \times 100\%.$$

The LHSV (hr$^{-1}$) is $$\frac{g/hr \, aqueous \, SN \, mixture}{cc \, catalyst}.$$

The percent SN; percent O$_2$; percent H$_2$O are each mole percent fed to the reactor as vapor, assuming no reaction takes place. The results obtained are given in Table II below.

TABLE II

| Run | Cat | % SN | % O$_2$ | % H$_2$O | Temp (°C.) | LHSV | Isomer Fraction | O$_2$ Conv. | SN Conv. | Sel. |
|---|---|---|---|---|---|---|---|---|---|---|
| A | SA | 4.48 | 2.30 | 2.75 | 400 | 0.32 | 55.9 | 100 | 38.1 | 72.0 |
| B | SA | 4.31 | 3.09 | 2.64 | 410 | 0.32 | 45.9 | 100 | 48.6 | 68.1 |

TABLE II-continued

| Run | Cat | % SN | % O$_2$ | % H$_2$O | Temp (°C.) | LHSV | Isomer Fraction | O$_2$ Conv. | SN Conv. | Sel. |
| --- | --- | --- | --- | --- | --- | --- | --- | --- | --- | --- |
| C | SA | 6.96 | 3.43 | 75.9 | 410 | 0.32 | very low conversion to FN and SN ~20% of unidentified product | | | |
| D | DA | 3.57 | 3.31 | 79.9 | 410 | 0.32 | 63.2 | 92.6 | 53.3 | 63.5 |
| E | DA | 6.96 | 3.43 | 75.9 | 410 | 0.32 | 60.0 | 99.8 | 29.5 | 59.2 |
| F | DA | 9.32 | 1.46 | 4.99 | 405 | 0.67 | 45.9 | 79.5 | 12.2 | 82.6 |
|   |    | 8.99 | 2.13 | 4.79 |     | 0.67 | 49.1 | 59.5 | 14.0 | 82.9 |
|   |    | 8.59 | 2.90 | 4.59 |     | 0.67 | 50.4 | 55.5 | 15.8 | 77.1 |
| G | DA | 3.71 | 2.66 | 83.0 | 410 | 0.32 | 61.5 | 97.8 | 46.7 | 66.8 |
| H | DB | 7.37 | 3.78 | 4.49 | 405 | 0.32 | 49.0 | 76.1 | 26.7 | 68.4 |
|   |    | 9.29 | 2.12 | 5.65 |     | 0.71 | 45.9 | 71.8 | 15.0 | 80.1 |
|   |    | 9.62 | 1.45 | 5.87 |     | 0.71 | 44.0 | 89.5 | 14.1 | 57.1 |
| I | DB | 7.37 | 3.78 | 4.49 | 410 | 0.32 | 49.0 | 74.3 | 28.8 | 72.6 |
|   |    | 9.86 | 5.06 | 6.01 |     | 0.32 | 50.6 | 85.0 | 28.6 | 66.0 |
|   |    | 8.96 | 6.42 | 5.46 |     | 0.32 | 42.9 | 75.1 | 30.1 | 57.1 |
| J | DS | 8.98 | 2.13 | 4.79 | 401 | 0.67 | 47.8 | 87.2 | 19.4 | 81.1 |
|   |    | 8.00 | 2.81 | 4.27 | 410 | 0.32 | 50.7 | 100  | 27.0 | 70.3 |
|   |    | 7.54 | 3.84 | 4.03 | 410 | 0.32 | 50.0 | 87.3 | 29.9 | 67.4 |

EXAMPLE 5 - Preparation of α-Bi$_2$Mo$_3$O$_{12}$

A 31.8-g portion of (NH$_4$)$_6$Mo$_7$O$_{24}$ is dissolved in 400 ml water. A 58.2-g portion of Bi(NO$_3$)$_3$ is dissolved in 60 ml concentrated nitric acid and diluted to 2340 ml. Concentrated nitric acid is added to the molybdenum solution until its pH is 1.5. At about a pH of 2.0, precipitation begins. The precipitate is allowed to age about 1.5 hours and then the bismuth solution is added while 88 ml concentrated ammonia is co-fed to maintain the pH at 1.42 to 1.56. The precipitate is allowed to stand overnight and is then collected by filtration. The collected precipitate is calcined in air for 5 hours at 200° C. and then the temperature is increased to 450° C. and it is calcined an additional 15 hours. The calcined α-Bi$_2$Mo$_3$O$_{12}$ is blended with a sufficient amount of clay so that the clay binder constitutes 20 percent of the catalyst. The catalyst with binder is then calcined for 2 hours at 200° C. and for an additional 4 hours at 500° C. The surface area of the final powder is 0.39 m$^2$/g.

EXAMPLE 6 - Preparation of Mixed Bi-Fe-Mo-O

The precipitate for α-Bi$_2$Mo$_3$O$_{12}$ is prepared as described in Example 5 with the exception that the precipitate is not collected by filtration. The mother liquor is drained off. A 24.24-g portion of Fe(NO$_3$)$_3$·9H$_2$O is dissolved in 400 ml water and concentrated ammonia is added to raise the pH of the solution to 3.1. The iron solution and the bismuth solution are added together and the excess water is boiled off. The resulting solid is calcined for 2 hours at 200° C. and for an additional 15 hours at 550° C. This calcined powder is mixed with 20 percent binder and calcined for 2 hours at 200° C. and then for an additional 4 hours at 500° C.

EXAMPLE 7 - Preparation of Bi$_3$FeMo$_2$O$_{12}$

The procedure described in Example 6 is followed using 87.3 g of Bi(NO$_3$)$_3$ dissolved in 90 ml of concentrated nitric acid and diluted to 2400 ml: 21.9 g (NH$_4$)$_6$Mo$_7$O$_{24}$ dissolved in 270 ml of water; 24.2 g Fe(NO$_3$·9H$_2$O dissolved in 400 ml of water with 12 ml of concentrated ammonia to raise the pH to 4.5. The final surface area of the calcined powder is 2.85 m$^2$/g.

EXAMPLE 8 - Preparation of Bi$_2$Fe$_2$Mo$_2$O$_{12}$

The procedure described in Example 6 is followed using 58.2 g of Bi(NO$_3$)$_3$; 21.2 g (NH$_4$)$_6$Mo$_7$O$_{24}$; and 48.5 g Fe(NO$_3$)$_3$·9H$_2$O. The final surface area of the calcined powder is 4.25 m$^2$/g.

EXAMPLE 9 - Preparation of Bi$_{1.8}$Ce$_{0.2}$(MoO$_4$)$_3$

A 69.85-g portion of Bi(NO$_3$)$_3$ is dissolved in 70 ml of concentrated nitric acid and diluted to 2400 ml while 42.37 g of (NH$_4$)$_6$Mo$_7$O$_{24}$ is dissolved in 530 ml of water. A bismuth molybdate precipitate is prepared as described in Example 1. (NH$_4$)$_2$Ce(NO$_3$)$_6$ (8.77 g) is dissolved in 160 ml water and a 25 percent ammonia solution is added to precipitate Ce at a pH of 4.10. The precipitates are dried as described in the previous examples and are mixed and calcined in air at 200° C. for 2 hours and then at 550° C. for an additional 15 hours. The calcined powder is blended with a 20 percent binder and calcined an additional 2 hours at 200° C. and for 4 hours at 500° C. The final surface area of the powder is 0.84 m$^2$/g.

EXAMPLE 10 - Preparation of Bi$_{0.875}$Ce$_{0.1.125}$(MoO$_4$)$_3$

The procedure outlined in Example 9 is followed using 33.96 g of Bi(NO$_3$)$_3$, 49.34 g of (NH$_4$)$_2$Ce(NO$_3$)$_6$ and 42.37 g of (NH$_4$)$_6$Mo$_7$O$_{24}$. The final surface area of the powder is 0.69 m$^2$/g.

EXAMPLE 11 - Preparation of Bi$_4$(ZnO$_4$)(MoO$_4$)$_3$

A 80.57-g portion of Bi(NO$_3$)$_3$ is dissolved in 80 ml of concentrated nitric acid and diluted to 2210 ml with water. Then, 22.0 g of (NH$_4$)$_6$Mo$_7$O$_{24}$ is dissolved in 400 ml of water. A precipitate is produced at a pH of about 1.3 to 1.6 as described in Example 1. The solution behaves as a buffer. The precipitate is left to stand about 12 hours and is then collected on a filter. A 9.11-g portion of Zn(C$_2$H$_3$O$_2$)$_2$·2H$_2$O is dissolved in 30 ml of water and added to the precipitate. The material is allowed to dry for about 48 hours. The dried powder is calcined at 200° C. for 2 hours and then at 450° C. for 15 hours. This calcined powder is mixed with a clay binder so that the mixture is 20 percent binder. Then the catalyst with binder is calcined at 200° C. for 2 hours and at 500° C. for an additional 4 hours. The surface area of the calcined catalyst is 6.03 m$^2$/g.

EXAMPLE 12 - Preparation of Fe$_2$Mo$_3$O$_{12}$

A 69.0-g portion of Fe(NO$_3$)$_3$·9H$_2$O is dissolved in 400 ml of water to yield 450 ml of solution. A 45.23-g portion of (NH$_4$)$_6$Mo$_7$O$_{24}$ is dissolved in 1200 ml of water. The molybdenum solution is acidified with 13.8 ml of concentrated nitric acid to lower the pH from 5.32 to 1.85. No precipitation occurs. The iron solution is then added to the molybdenum solution in a one-hour period. The pH drops to 1.47 and the solution is refluxed for 4 hours and then is allowed to stand for about 48 hours. A yellow green precipitate is present and is recovered by filtration. The powder is calcined at 200° C. for 2 hours and then at 430° C. for 3 hours. This calcined powder is mixed with a clay binder so that the mixture is 20 percent binder. Then the catalyst with binder is calcined at 200° C. for 2 hours and at 500° C. for an additional 4 hours. The surface area of the calcined catalyst is 6.95 m²/g.

EXAMPLE 13 - Preparation of Fumaronitrile and Maleonitrile

The general procedure of Example 4 is followed to prepare fumaronitrile and maleonitrile using various catalysts and temperatures. However, some of the details differ as shown below.

The reactor is a 0.5-inch o.d. by 30-inch 316 stainless steel tube containing 20 cubic centimeters of 5-12 mesh catalyst. A 0.25-inch thermowell is attached to the outside of the reactor tube and the operating temperature is measured by sliding a type K thermocouple inside the thermowell. Succinonitrile is added as a succinonitrile/water eutectic with about 91 percent succinonitrile and about 9 percent water. The liquid hourly space velocity is 0.3 g of the eutectic mixture per hour per cubic centimeter of catalyst. The molar ratio of oxygen to succinonitrile ranges from 1.4 to 1 7. The product from the reactor is collected in a receiver and liquid samples are analyzed with a capillary gas chromatograph. Noncondensed products are directed to an online gas chromatograph. This gas chromatograph analyzes for oxygen, nitrogen, carbon monoxide, carbon dioxide, ammonia, water and hydrogen cyanide. Deep oxidation losses are calculated from the analysis of noncondensed products and by assuming that succinonitrile oxidizes to carbon dioxide and ammonia, carbon dioxide and hydrogen cyanide, and carbon monoxide and hydrogen cyanide.

The results are given in Table III below. The conversion reported is the amount of succinonitrile consumed divided by the amount of succinonitrile fed multiplied by 100 to give the percentage. The selectivity reported is the amount of fumaronitrile and maleonitrile produced divided by the amount of succinonitrile converted and multiplied by 100 to give the percentage. In each run, the material is collected over a period of approximately two days. The variations in temperature, SCN converted and selectivity reflect differences obtained over time. The percentage of conversion and selectivity typically decay over time so that the higher numbers represent data collected at the beginning of each run and the lower numbers represent data collected at the end of each run.

TABLE III

| Catalyst | Temp (°C.) | SCN Converted | Selectivity |
|---|---|---|---|
| α-Bi$_2$Mo$_3$O$_{12}$ | 400–407 | 25–28 | 69–73 |
| Mixed Bi-Fe-Mo-O | 410–418 | 58–62 | 58–60 |
|  |  | 51–54 | 47–55 |
| Bi$_3$FeMo$_2$O$_{12}$ | 395–405 | 37–39 | 67 |
|  | ~415 | 63–64 | 61 |
| Bi$_2$Fe$_2$Mo$_2$O$_{12}$ | 370 | 59 | 64 |
| Bi$_{1.8}$Ce$_{0.2}$(MoO$_4$)$_3$ | 400–410 | 14–16 | 59–61 |
| Bi$_{0.875}$Ce$_{1.125}$(MoO$_4$)$_3$ | 400–410 | 10–16 | 65–68 |
| La$_2$Mo$_3$O$_{12}$ | 400 | 28–31 | 70–72 |
|  | 425 | 51–53 | 70–72 |
| Bi$_4$(ZnO$_4$)(MoO$_4$)$_3$ | 400 | 28–35 | 69–73 |
| Fe$_2$Mo$_3$O$_{12}$ | 375 | 30 | 45 |

TABLE III-continued

| Catalyst | Temp (°C.) | SCN Converted | Selectivity |
|---|---|---|---|
| DA | 406–415 | 38–46 | 74–78 |
| DS | 405–418 | 49–55 | 77–81 |

The information in Table III above clearly demonstrates that the process for the oxydehydrogenation of saturated dinitriles to form unsaturated dinitriles using the specified catalysts results in relatively high conversions of saturated dinitriles with good selectivity to the unsaturated dinitriles.

EXAMPLE 14 - Preparation of Catalysts with K$_2$CO$_3$

The catalysts are prepared as described in the above examples with the exception that K$_2$CO$_3$ is dry blended with the calcined catalyst powder prior to the addition of binder and the final calcination. The amount of K$_2$CO$_3$ used is specified in Table II below.

The procedures given in Example 13 are followed for the preparation of fumaronitrile and maleonitrile and the results obtained are given in Table IV below.

TABLE IV

| Catalyst | K$_2$CO$_3$ (Wt. %) | Temp (°C.) | SCN Converted | Selectivity |
|---|---|---|---|---|
| Bi$_2$Fe$_2$Mo$_2$O$_{12}$ | 0 | 375 | 40 | 58 |
|  | 1 | 370–380 | 51–55 | 67–69 |
|  | 4.3 | 370 | 45–55 | 64–66 |
|  | 10 | 375 | 58 | 65 |
| Bi$_4$(ZnO$_4$)(MoO$_4$)$_3$ | 0 | 400 | 28–35 | 69–73 |
|  | 10 | 390–400 | 58–68 | 66 |
| Dow A | 0 | 406–415 | 38–46 | 74–78 |
|  | 1 | 405–408 | 36–53 | 75–81 |
|  | 5 | 407–414 | 48–68 | 69–76 |
|  | 10 | 400 | 47–53 | 68–71 |
|  | 20 | 250 | 26–41 | 53–59 |

The information in Table IV above clearly demonstrates the effectiveness of K$_2$CO$_3$ in improving the catalyst activity. When the catalyst used is Bi$_2$Fe$_2$Mo$_2$O$_{12}$, the addition of K$_2$CO$_3$ results in increased conversion and selectivity. When the catalyst used is Bi$_4$(ZnO$_4$)(MoO$_4$)$_3$, selectivity is not improved, but conversion is substantially increased. When the catalyst used is the Dow A type, selectivity is substantially improved.

What is claimed is:

1. A process for the preparation of an unsaturated dinitrile selected from the group consisting of fumaronitrile and substituted fumaronitrile and maleonitrile and substituted maleonitrile corresponding to the formula:

$$N \equiv CCR^1 = CR^2C \equiv N$$

wherein $R^1$ and $R^2$ are separately at each occurrence hydrogen or methyl by the oxydehydrogenation of succinonitrile corresponding to the formula:

$$N \equiv CCHR^1 - CHR^2C \equiv N$$

wherein $R^1$ and $R^2$ are separately at each occurrence hydrogen or methyl, said process comprising contacting, in the presence of water, oxygen and the saturated dinitrile in a mole ratio of O$_2$ to unsaturated dinitrile in the in the range of about 0.1:1 to about 5:1 and with a water content of the feed in the range of form about 3 to about 90 weight percent, said contact being in the presence of a catalyst selected from the group consisting of strontium nickel phosphate and calcium nickel phosphate and at a temperature above about 50° C. and below about 600° C. and a pressure in the range of from about 0.5 to about 10 atmosphere.

2. The process of claim 1 wherein the catalyst additionally contains an alkali metal.

3. The process of claim 2 wherein the alkali metal is selected from the group consisting of potassium, sodium and cesium.

4. The process of claim 2 wherein the alkali metal is potassium.

5. The process of claim 1 wherein the catalyst is unsupported.

6. The process of claim 1 wherein the catalyst further comprises a binder.

7. The process of claim 6 wherein the binder is selected from the group comprising silica, titania, aluminum phosphate, kaolin clay, mortmorillonite clay, attapulgite clay and Portland cement.

8. The process of claim 7 wherein the binder is kaolin clay.

9. The process of claim 7 wherein the binder is used in an amount of at least about 1 weight percent and no greater than about 60 weight percent based on the weight of the catalyst compound and binder.

10. The process of claim 9 wherein the binder is used in an amount of at least about 10 weight percent and no greater than about 30 weight percent based on the weight of the catalyst compound and binder.

11. The process of claim 1 wherein the catalyst is calcined.

12. The process of claim 6 wherein the catalyst is calcined.

13. The process of claim 2 wherein the alkali metal salt is used in an amount of at least about 0.1 weight percent and no greater than about 20 weight percent based on the total weight of the catalyst.

14. The process of claim 13 wherein the alkali metal salt is used in an amount of at least about 1.0 weight percent and no greater than about 10 weight percent based on the total weight of the catalyst.

15. The process of claim 14 wherein the alkali metal salt is used in an amount of no greater than about 5 weight percent based on the total weight of the catalyst.

* * * * *

UNITED STATES PATENT AND TRADEMARK OFFICE
CERTIFICATE OF CORRECTION

PATENT NO. : 5,013,860
DATED : May 7, 1991
INVENTOR(S) : Harold W. Young, Jr., William P. Dianis It is certified that error appears in the above-identified patent and that said Letters Patent is hereby corrected as shown below:

Column 16, line 59, "$N=CCHR^1-CHR^2C=N$", should correctly read --$N\equiv CCHR^1-CHR^2C\equiv N$--.

Signed and Sealed this

Twenty-second Day of December, 1992

*Attest:*

DOUGLAS B. COMER

*Attesting Officer*     *Acting Commissioner of Patents and Trademarks*